United States Patent [19]

Becker

[11] Patent Number: 5,507,808
[45] Date of Patent: Apr. 16, 1996

[54] FILLING TUBE AND SEAL CONSTRUCTION

[76] Inventor: Hilton Becker, 5458 Town Ctr. Rd., Boca Raton, Fla. 33486

[21] Appl. No.: 329,179

[22] Filed: Oct. 26, 1994

[51] Int. Cl.[6] .................................................. A61F 2/12
[52] U.S. Cl. ................................................. 623/8; 251/349
[58] Field of Search .................... 623/8; 251/349; 606/191, 198; 604/96, 97

[56] References Cited

U.S. PATENT DOCUMENTS

| | | | |
|---|---|---|---|
| 2,183,900 | 12/1939 | Voit et al. | 251/349 |
| 2,698,436 | 1/1955 | Bernhardt . | |
| 2,704,622 | 3/1955 | Soffer | 251/349 |
| 3,600,718 | 8/1971 | Boone . | |
| 3,852,832 | 12/1974 | McGhan et al. | 623/8 |
| 3,883,902 | 5/1975 | Lynch . | |
| 3,919,724 | 11/1975 | Sanders et al. | 623/8 |
| 4,190,040 | 2/1980 | Schulte . | |
| 4,643,733 | 2/1987 | Becker . | |
| 4,662,357 | 5/1987 | Pierce et al. | 623/8 |
| 4,662,883 | 5/1987 | Bell et al. | 623/8 |
| 4,773,908 | 9/1988 | Becker . | |
| 4,944,749 | 7/1990 | Becker . | |
| 4,969,899 | 11/1990 | Cox | 623/8 |
| 5,083,576 | 1/1992 | Ruiz-Razura et al. . | |
| 5,146,933 | 9/1992 | Boyd | 623/8 |

FOREIGN PATENT DOCUMENTS 789206  7/1968  Canada .

Primary Examiner—David H. Willse
Assistant Examiner—Bruce E. Snow
Attorney, Agent, or Firm—Bacon & Thomas

[57] ABSTRACT

An inflatable implant for use in human breast reconstruction includes a chamber which is defined by a flexible membrane. The implant also includes a valve and a flexible filling tube which passes through the valve and into the chamber. The valve comprises a short semi-rigid tube that surrounds an opening in the membrane and extend inwardly of the membrane and into the chamber. The semi-rigid tube defines a passageway extending therethrough and also defines a relatively small reservoir which opens into the passageway. A filling tube comprises a soft and flexible length of tubing and a solid portion has an outer diameter which is slightly larger than the inner diameter of the semi-rigid tube and is stretchable longitudinally to reduce its outer diameter to facilitate passage through the semi-rigid tube. And the solid portion is adapted to sealingly engage the semi-rigid tube upon relaxation thereof.

7 Claims, 1 Drawing Sheet

FILLING TUBE AND SEAL CONSTRUCTION

BACKGROUND OF THE INVENTION

Field of the Invention

This invention relates to an improved filling tube and seal construction for inflatable implants and more particularly to a filling tube and seal construction for use in inflatable implants of the type used in breast reconstruction.

An inflatable implant for use in human breast reconstruction includes at least one and at times two chambers. The chambers are defined by a flexible membrane or lumen and includes valves which are adapted to have a single flexible filling tube passed therethrough for filling the inner chamber.

A dual chamber device includes a viscous gel in the outer chamber as disclosed in my U.S. Pat. No. 4,773,908 which is incorporated herein in its entirety by reference. The viscous gel which has in the past comprised a silicon gel is in contact with the valves and sealingly cooperates with the valves and the filling tube.

The implant also includes at least one valve having a short semi-rigid tube surrounding an opening and extending inwardly of the membrane, i.e., into the chamber. The filling tube comprises a soft and flexible length of tubing and a solid portion has an outer diameter which is slightly larger than the inner diameter of the semi-rigid tube and is stretchable longitudinally to reduce its outer diameter to facilitate passage through the semi-rigid tube. The solid portion is adapted to sealingly engage the semi-rigid tube upon relaxation thereof.

A recent increase in the demand for saline filled implants, as opposed to silicon filled implants, has led to a need for an improved valve and seal construction. Such constructions should minimize the likelihood of leakage of the saline or gel into the human body. The improved valve and seal construction should minimize any discomfort to the patient, be relatively inexpensive to manufacture, facilitate injection of a saline or other material into the implant and automatically and securely close the valve after injection of the saline solution into the implant.

It is presently believed that the valve and seal construction in accordance with the present invention offers a significant improvement over the device which is disclosed in my previously mentioned patent and will have the aforementioned advantageous features.

BRIEF SUMMARY OF THE INVENTION

The present invention relates to a filling tube and seal construction for an inflatable prosthesis. The prosthesis includes at least one flexible lumen or chamber which is adapted to be filled with an inflating fluid. The wall of this lumen is made of a membrane and defines an inlet opening through which the lumen is inflated. A semi-rigid tube having an inner passageway surrounds the opening and extends inwardly into the lumen. The semi-rigid tube also opens into and/or defines a reservoir which is disposed between the ends thereof and includes an opening into the passageway. A filling tube including a flexible length of tubing passes through the semi-rigid tube and extends inwardly into the interior of the lumen. The outer diameter of this filling tube is slightly larger than the inside diameter of the semi-rigid tube. And, the filling tube is stretchable longitudinally to reduce its outer diameter to facilitate the insertion or passage of a distal end of the filling tube through the semi-rigid tube. The filing tube is also adapted to sealingly engage the semi-rigid tube upon the relaxation thereof and has at least one opening therein for insertion of fluid into the lumen.

In addition, the distal end of the filling tube which extends into the interior of the prosthesis, defines or forms a solid portion. And after inflation of the lumen, the filling tube is stretched longitudinally and pulled outwardly through the rigid tube until the solid portion thereof is encompassed by the rigid tube to thereby seal the opening when the stretched tube is allowed to relax.

The portion of the filling tube that extends outwardly from the lumen is adapted to be cut off adjacent to the outer end of the semi-rigid tube and forms a relatively smooth surface therewith.

The accompanying drawings, which are incorporated in and constitute a part of this specification, illustrate the preferred embodiments of the invention and, together with the description, serve to explain the principles of the invention.

DETAILED DESCRIPTION OF THE PREFERRED EMBODIMENT OF THE INVENTION

Figure 1:
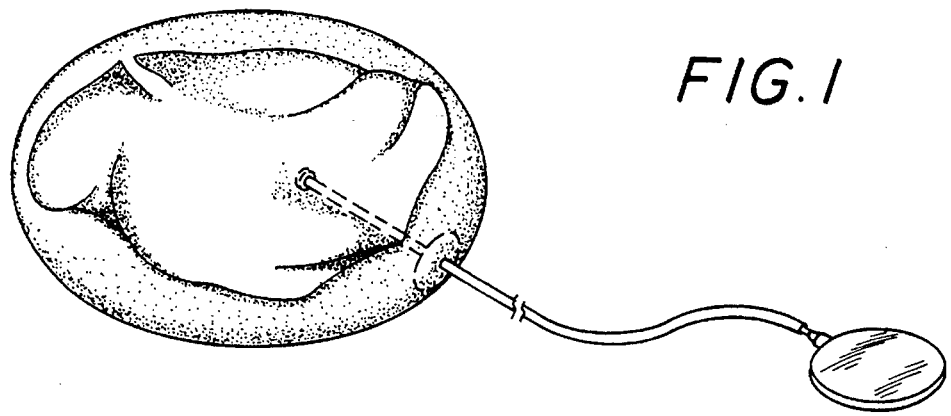
FIG. 1 is a perspective view illustrating a single lumen inflatable prosthesis embodying a preferred form of a filling tube and seal construction according to the present invention and shown with a filling tube and an attached injection dome in place for inflating the prosthesis.
Figure 2:
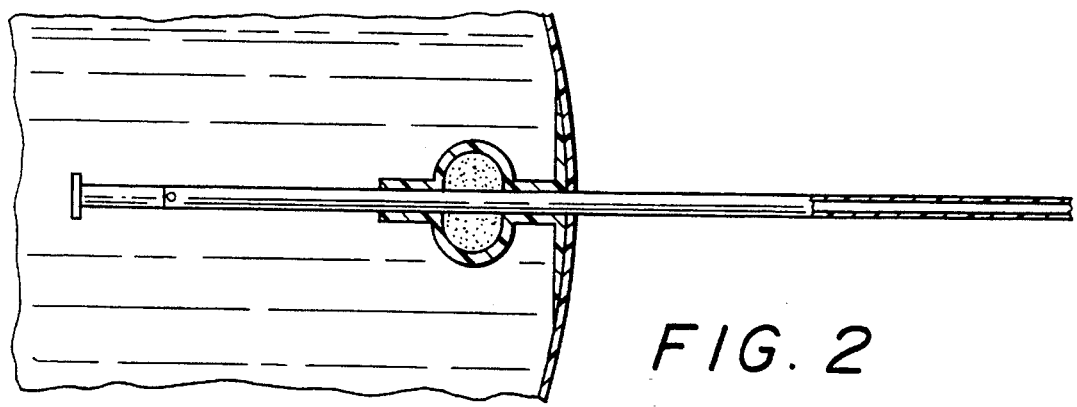
FIG. 2 is an enlarged view of a portion of FIG. 1 showing the filling tube in position for inflating the prosthesis.
Figure 3:
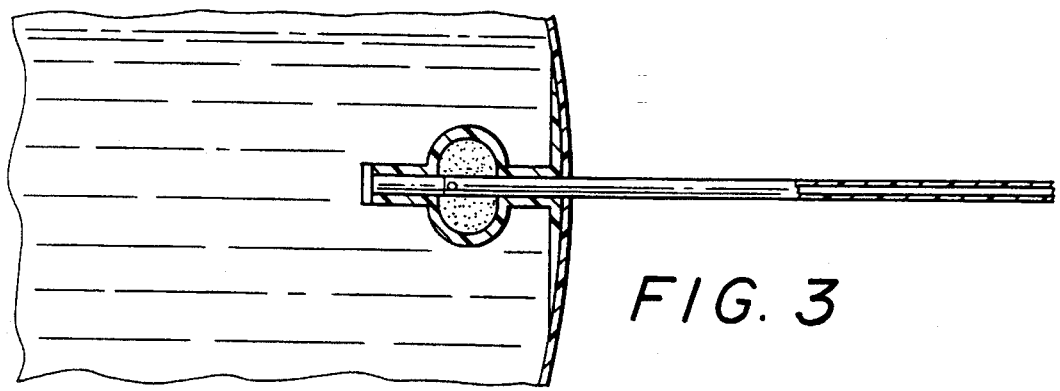
FIG. 3 is an enlarged view of a portion of FIG. 1 showing the filling tube in position for sealing the prosthesis.

References will now be made in detail to the embodiments of the invention, examples of which are illustrated in the accompanying drawings. A preferred embodiment, i.e., best mode, of the filling tube and seal construction is shown in FIG. 1–3. In accordance with the invention, a filling tube and seal construction is embodied in an inflatable device such as an inflatable implant 13 which includes at least one flexible membrane or lumen 15. The flexible membrane or lumen 15 defines an inflation chamber 16 which is adapted for filling with a fluid to thereby inflate the implant 13. The lumen 15 also defines an inlet opening 17 through which an inflating fluid is delivered (see FIG. 2).

In accordance with the invention, the filling tube and seal construction includes a semi-rigid tube 18 which has a relatively thick wall with respect to the thickness of the membrane and which surrounds the opening 17. The tube 18 extends inwardly of the lumen 15, and has a passage 23 therethrough which opens inside of the lumen 15.

The lumen 15 is constructed of a suitable material or membrane such as a medical grade silicone elastomer or similar material which does not react with human tissue, as will be understood by those skilled in the art. And, the short semi-rigid tube 18 may be formed of the same or of a different material but is preferably formed as an integral part of the membrane and derives its semi-rigid characteristic from the thickness of its wall section. It may also be desirable to form a thicker portion 19 of the lumen 15 as illustrated to further support the tube 18. This thickened portion 19 surrounds the opening 17 and reduces the likelihood of any breaking or tearing of the membrane.

The semi-rigid tube 18 also defines a reservoir R which is open to an inner passageway or passage 23 of the semi-rigid tube 18. For example, the reservoir R may take the form of an outwardly extending bulge like projection which defines a reservoir with a portion thereof opening into the passage 23. The reservoir R is preferably filled with a sealant or gel S such as a silicon gel.

It is presently believed, particularly in view of the more recent studies that the small amount of silicon gel contained in the reservoir poses no risk to a recipient of an implant. However, if there is a concern about the use of a silicon gel, other naturally occurring gels which are compatible with human tissue and which will be absorbed by the human body such as peanut oil can be used.

A filling tube 27 constructed of silicone tubing or the like is adapted to pass through the passage 23 which is defined by the relatively short, semi-rigid tube 18. The filling tube 27 also includes a solid distal portion 28, which is preferably slightly longer than the length of the semi-rigid tube 18, and a proximal portion 29 which defines a hollow passageway 30 and an opening 32. The opening 32 connects the passageway 30 with the interior of the chamber 16 and operatively connects the interior of the chamber 16 to an injection dome or reservoir 34.

The filling tube 27 is relatively soft so as not to puncture or damage the tube 18 or the lumen 15. This filling tube 27 has an outer diameter which is slightly larger than the inside diameter of the passageway 23 and is stretchable in the longitudinal direction to reduce its outside diameter. Reduction of the outside diameter facilitates the passage of the filling tube 27 through the semirigid tube 18. And the solid portion 28 of the filling tube is adapted to sealingly engage the passageway 23 in the semi-rigid tube 18 upon relaxation from a stretched condition.

In practice, the filling tube may be forced through the passageway 23 by means of a rigid member (not shown) or could be molded into place by having the lumen and semi-rigid tube molded around the filling tube. In the latter case, the filling tube would include an area of reduced diameter so that the inside diameter of the tube 18 would be smaller than the outside diameter of at least the solid portion 28 of the filling tube 27.

The proximal end 27' of the tube 27 is adapted for connection to a fluid source such as the reservoir 34. Fluid such as a saline solution is then forced from the reservoir 34 by means of a hypodermic needle inserted therein (not shown) through the passageway 30 and opening 17 and into the chamber 16. When the chamber 16 is sufficiently filled, the filling tube is stretched longitudinally by pulling and passes through the passageway 23 until the solid distal portion 28 is encompassed by the semi-rigid tube 18. When the pressure or longitudinal extension is released, the solid distal portion returns to its original outside diameter and together with the gel S in reservoir R sealingly engages the semi-rigid tube 18.

In a preferred embodiment of the invention, the solid distal portion 28 includes a generally radially extending flange 35 having a generally T-shaped cross section for engaging a seat 36 on the semi-rigid tube 18. This radially extending flange acts as a stop means and prevents the filling tube 27 from being pulled through the semi-rigid tube 18 and contributes to the reliability of the seal.

Various factors must be considered in constructing the filling tube and seal or valve, such as the thickness of the semi-rigid tube, the stiffness of the materials, the lengths of the semi-rigid tube and the filling tube, their diameters including the nature of the fluids contained within the implant, viscosity of the sealant in the reservoir, the pressure of the fluid, etc. Those skilled in the art will appreciate that the seal must not leak and must not cause discomfort to the patient.

Figure 4:
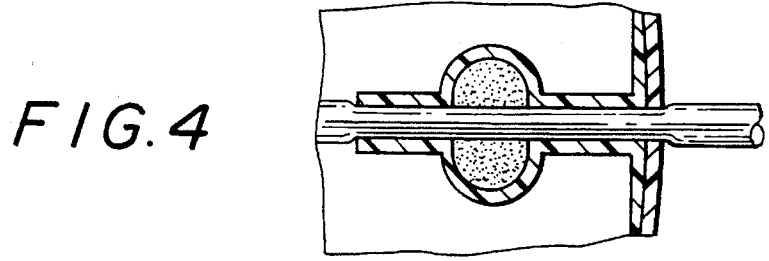
FIG. 4 is an enlarged view of the filling tube and sealing construction according to one embodiment of the invention.

FIG. 4 illustrates a second embodiment of the invention wherein filling tube 27 is manufactured with a portion 22' of reduced diameter. This further reduction in diameter should minimize any likelihood of leakage during shipment and storage and facilitate forming tubular element 18 around filling tube 27 during the manufacturing operation.

It will also be appreciated that inflatable prosthesis of this type often have the filling tube inserted in place at the time the prosthesis is manufactured and prior to packaging. Thus, the filling tube remains in place during the entire shelf life of the prosthesis which can be for a considerable length of time. A number of previous valves acquired a "set" during this time so that when the prosthesis was implanted, expanded, and the filling tube removed, leakage occurred at the valve. This problem was remedied by incorporating a kink or curled valve into the system. However, the complexity of manufacture adds to the cost of the device. Furthermore, the curled valve can often be felt by the patient. It is presently thought that the present invention will overcome this tendency and as such constitutes an improvement on the valves disclosed in my earlier patent.

It is also believed that the contact of the gel used as a sealant with a portion of the filling tube will act on the filling tube to further maintain its flexibility and at the same time provide a lubricant which makes it easier to pull the filling tube through the semi-rigid tube and into its closed position. In other words, it will be less likely that the step of closing the chamber will dislodge the implant or damage the membrane.

While the invention has been described in connection with its preferred embodiments, it should be recognized that change and modifications may be made without departing from the scope of the appended claims.

What is claimed is:

1. A filling tube and seal construction for an inflatable implant which includes a chamber defined by a flexible membrane, said construction comprising means defining an inlet opening in said chamber and a semi-rigid tube surrounding said inlet opening and extending inwardly into said chamber, said semi-rigid tube defining a longitudinally extending passageway with a near end adjacent to and abutting said inlet opening and a far end within said chamber, said semi-rigid tube further defining a reservoir which is spaced from said flexible membrane and which opens into said passageway, and a mass of sealant contained within said reservoir, a filling tube comprising a soft and flexible length of tubing forming a solid portion at a distal end thereof, said solid portion being longer than said semi-rigid tube, and the remaining portion of said filling tube defining a second hollow passageway and an opening for connecting the interior of said filling tube with the interior of said chamber for inflation of said chamber, and said filling tube having an outer diameter large than the inner diameter of said semi-rigid tube and being stretchable longitudinally to reduce its outer diameter to facilitate passage through said semi-rigid tube, said solid portion of said filling tube sealingly engaging said semi-rigid tube upon relaxation therein in contact with said sealant in said reservoir whereby said filling tube can be stretched longitudinally and moved outwardly through said semi-rigid tube by pulling on a proximal portion of said filling tubes after inflation of said chamber to position said solid portion in said semi-rigid tube in contact with said mass of sealant to seal said opening in said membrane.

2. The tube construction called for in claim 1 in which said filling tube includes means at the distal end thereof engageable with said semi-rigid tube to limit withdrawal of said filling tube.

3. The construction called for in claim 2 in which said limiting means has a generally T-shaped cross-section.

4. The construction called for in claim 2 in which said distal end means includes a generally radially extending flange engageable with said semi-rigid tube.

5. The construction called for in claim 4 in which said filling tube is made of silicone elastomer.

6. The construction called for in claim 5 in which the membrane and semi-rigid tube are made of a silicone elastomer and said semi-rigid tube is formed as an integral part of said membrane.

7. The construction called for in claim 6 in which said membrane includes a thicker portion adjacent said semi-rigid tube to thereby reduce the likelihood of tearing the membrane in that area.

* * * * *